United States Patent [19]

Hardenbrook et al.

[11] Patent Number: 5,063,297

[45] Date of Patent: * Nov. 5, 1991

[54] APPARATUS FOR DETECTING FLUORESCENCE OF A LUMINESCENT MATERIAL

[75] Inventors: James M. Hardenbrook, Longwood; Richard E. Williams, Lake Mary; Mark L. Daniel, Deltona, all of Fla.

[73] Assignee: Minnesota Mining and Manufacturing Company, St. Paul, Minn.

[*] Notice: The portion of the term of this patent subsequent to Jul. 9, 2008 has been disclaimed.

[21] Appl. No.: 515,203

[22] Filed: Apr. 27, 1990

Related U.S. Application Data

[63] Continuation-in-part of Ser. No. 364,194, Jun. 8, 1989, Pat. No. 5,030,832.

[51] Int. Cl.[5] .................................................. G01J 1/58
[52] U.S. Cl. ................................ 250/458.1; 250/461.1
[58] Field of Search ............... 250/458.1, 459.1, 461.1, 250/461.2, 361 R, 361 C

[56] References Cited

U.S. PATENT DOCUMENTS

4,945,245   7/1990   Levin ............................. 250/461.1

Primary Examiner—Edward P. Westin
Assistant Examiner—Richard Hanig
Attorney, Agent, or Firm—Gary L. Griswold; Walter N. Kirn; William D. Bauer

[57] ABSTRACT

An apparatus for detecting the fluorescence of a luminescent material. Photo-semiconductors receiving the visible fluorescence from a target luminescent material and directly from a discharge lamp are electrically coupled to oppose each other resulting in a single-channel detector inherently balanced and insensitive to variations in the excitation stimulus. The photo-semiconductor output is sent through a second harmonic amplifier making available a phase detection of the fluorescence instead of an amplitude detection. The phase of the signal is compared with a known phase from the excitation power source. By adding signals that either reinforce or oppose, the phase information is converted back to amplitude information at a voltage level that can be easily detected. The compared output then triggers an indicator producing an indication of the amount of fluorescence of the target luminescent material.

14 Claims, 2 Drawing Sheets

APPARATUS FOR DETECTING FLUORESCENCE OF A LUMINESCENT MATERIAL

RELATION APPLICATION

This application is a continuation-in-part of U.S. Ser. No. 07/364,194, Williams et al, Apparatus for Detecting Fluorescence of a Luminescent Material, filed June 8, 1989 now U.S. Pat. No. 5,030,832.

BACKGROUND OF THE INVENTION

The present invention relates generally to apparatus for detecting fluorescence of a luminescent material and more particularly to such apparatus utilizing an alternating current line voltage power source.

There are many environments where the sterilization of articles is of critical importance. Hospitals and medical offices must sterilize certain equipment before that equipment can be utilized with surgical procedures or in sterile environments. Also food service environments must take care that their utensils and equipment are sterilized in order to prevent subsequent possible infection of later users.

Commonly the equipment, instruments or materials that are to be sterilized may be subjected to the necessary parameters to achieve sterilization including the interrelated parameters of time, temperature, steam, dry heat, chemicals such as ethylene oxide gas or radiation dosage. The sterilization process is designed to kill living organisms which might otherwise contaminate the goods being sterilized. Steam sterilization ranges from 121-132 degrees Centigrade with exposure times of three minutes at 132 degrees Centigrade to 30 minutes at 121 degrees Centigrade Ethylene oxide sterilization ranges from 30-56 with exposure times of one hour to 65 degrees Centigrade to four hours at 30 degrees Centigrade. Dry heat sterilization typically is two hours at 180 degrees Centigrade.

Since it is critical in many environments that the sterilization be complete, frequently sterilization monitors are utilized. Typically, a small vial, or other container, is inserted into the sterilization unit in order to check upon the completeness of the sterilization process. The vial typically will contain living organisms that are provided nourishment and an environment for rapid growth after being subjected to the sterilization process.

The vial can then be checked for growth of the organism after a incubation period. The incubation allows any organism surviving the sterilization process to grow to a detectable level. Survival of the organism indicates an inadequate sterilization process.

In order to properly detect living organisms, typically a substrate material is added to the vial for the living organisms to react with causing the substrate to change color.

Typically, the reading or analysis of the color change has been done manually with observation by the human eye. However, in one sterilization monitor process, a potentially luminescent substrate material is added to the vial for the living organisms to react with. After allowing for a suitable reaction period, the vial is subjected to a fluorescent light, typically an ultraviolet wavelength light, which excites the invisible to the naked eye fluorescence to appear as visible light. The appearance of visible light in the vial when subjected to an exciting fluorescent light would indicate inadequate sterilization, due at least in part to a shortened time period required for the growth of the living organisms, more automated fluorescence detectors are to be utilized.

Further to more rapidly determine the completeness of the sterilization process, it is desired that fluorescence from the luminescent substrate in the vial be measured at a very low threshold, approximately 0.1 picowatt.

Unfortunately, the ultraviolet light source typically used tends to be very unstable due in part to variances in the gas ionization at one or more of the cathodes located at each end of the ultraviolet light source. Further, localized heat variations and emission fluctuations cause the output of the ultraviolet light source (lamp) to contain many independently varying harmonics of the power line frequency. The overall crest-to-trough ratio fluctuates similarly. The use of DC coupled amplifiers with low pass filtering to remove these fluctuations is unacceptable because the DC drift would be well in excess of the signal level being measured.

Some detectors attempt to solve this problem by either optically or electrically chopping the ultraviolet source to obtain an AC carrier for the signal. The AC carrier then is sometimes used in a dual channel device which provides an amplitude comparison channel providing a calibrated reference.

Alternatively, some detectors rely upon the short term stability of the DC drift and compensate for the drift by taking a reference reading and comparing the reference to the signal shortly thereafter.

However, a further problem exists when dual channels are utilized or when the target measurement is taken at a different time from the reference. Since, the signal being measured is so small, minor variations in components between dual channels, even with costly matched components, and between different times of measurement can result in a complete "swamping" of the signal to be measured. The result can easily be an inaccurate measurement. In order to compensate for the inherent inaccuracies in measurement, the "growth" period must be expanded (or not reduced) in order to ensure that living organisms, if present, will be detected.

Several prior United States patents disclose systems, all of which have one or more of the preceding problems.

U.S. Pat. No. 4,006,360, Mueller, discloses a system and method for determining the fluorescent emission from dye molecules bound to biological particles upon appropriate excitation. The system and method relies upon differing lifetimes of the excited state of the dye molecules. The stimulating radiation is cycled rapidly "on" and then "off" and the fluorescent emission is thereafter monitored. Light from the irradiated sample is passed through an optical passband filter and thereafter monitored by conventional photoelectric systems such as a photomultiplier.

U.S. Pat. No. 4,626,684, Landa, discloses an apparatus for rapidly conducting fluorescence measurements. The electronics of the apparatus utilizes dual channels. One channel detects the fluorescence of the sample. The other channel detects the fluorescence of a reference. The "background" reference fluorescence is subtracted from the signal sample in order to account for the background. However, in order for the reference to be effectively canceled the dual channels must be exactly matched U.S. Pat. No. 4,668,868, Noller, discloses a fluorescence detector for performing fluoroimmunoassays of biological specimens. The light energy from the sample is used to excite a photovoltaic cell. Temperature compensation is provided by a second photovoltaic cell from which light excitation is eliminated. A push button calibrator also used to provide a bias voltage from the voltaic cell with zero input signal which is memorized. A significant disadvantage of the system of Noller is the lack of a reference value. Since fluctuations in the intensity of stimulating radiation may greatly affect the amount of visible light output apparently perceived can vary greatly.

U.S. Pat. No. 4,750,837, Gifford et al, discloses a fluorometer with a reference light source. The system utilizes a pair of reference light pulses spaced between a pair of excitation light pulses. A microprocessor then reads these four electrical pulses and calculates the resulting concentration. This system is very complicated utilizing not only a plurality of excitation pulses and a pair of reference pulses but also a microprocessor in order to calculate the result.

SUMMARY OF THE INVENTION

The present invention provides an improved fluorescence detector. By providing an accurate analysis of the visible light produced by the luminescent material in response to the fluorescent stimulating radiation, a rapid, accurate determination can be made of the completeness of the sterilization. The detector of the present invention can reduce the wait required for the "growth" stage from a day, or more, to approximately fifteen (15) minutes. Possibly, even shorter wait times, could be achieved by the detector of the present invention.

The present invention solves the problem of having unmatched components in dual channels is solved by having only one channel. The reference determination is made by a photo-semiconductor which offsets the target determination, usually a photo-diode responsive to the fluorescing material. The opposing circuit arrangement eliminates the dual channels since all of the determination is made in a single channel.

In a preferred embodiment of the present invention the problem of variations in light source intensity is solved by AC coupling in order to eliminate the DC drift and in the use of the first harmonic of the power line frequency, namely 120 Hertz for the standard preferred 60 Hertz of the power line. It has been found that the first harmonic is relatively stable compared with variations in the fundamental frequency of the power line or in the higher order harmonics.

The present invention also helps eliminate the problems of component mismatch, uneven aging and temperature related changes of the components. The current produced by one photo-semiconductor does not have to flow through the high impedance of a second photo-semiconductor thus improving the sensitivity of the detecting circuitry while maintaining compensation for ambient temperature and compensation for variations in the output of the discharge lamp.

Thus, in one embodiment, the present invention provides an apparatus for detecting the fluorescence of a target luminescent material being excited at an excitation wavelength and fluorescing at a fluorescing wavelength. The apparatus utilizes a discharge lamp adapted to be coupled to an alternating current voltage source operating at a source frequency and arranged to excite the target luminescent material and the reference luminescent material at approximately the excitation wavelength. A first response mechanism is arranged to be responsive to the target luminescent material at approximately the fluorescing wavelength in order to provide a first electrical response as a function of the electromagnetic energy received from the target luminescent material at the fluorescing wavelength. A second response mechanism is arranged to be responsive to the discharge lamp in order to provide a second electrical response as a function of the electromagnetic energy received from the discharge lamp. The first response mechanism and the second response mechanism are arranged such that the first electrical response opposes the second electrical response creating a combined output signal. A band pass filter is coupled to the combined output signal and selected to pass predominantly signals of a frequency of approximately twice the source frequency to produce a filtered output signal. A phase detector is coupled to the band pass filter to detect the phase of the filtered output signal and produce a first response when the filtered output signal is of a first phase and produce a second response when the filtered signal is of a second phase. An indicator is coupled to the phase detector in order to indicate the condition of the fluorescence of the target luminescent material as a function of at least one of the first response and second response.

In a preferred embodiment of the present invention, the first response means and said second response means are first and second photo-semiconductors operating in photo voltaic mode and are oppositely coupled in parallel.

In another embodiment, the present invention provides an apparatus for detecting the fluorescence of a target luminescent material being excitable at an excitation wavelength and fluorescing at a fluorescing wavelength. A discharge lamp is adapted to be coupled to an alternating current voltage source operating at a source frequency and arranged to excite the target luminescent material at approximately the excitation wavelength. A first response mechanism is arranged to be responsive to the target luminescent material at approximately the fluorescing wavelength and provides a first electrical response as a function of the electromagnetic energy received from the target luminescent material at the fluorescing wavelength. A second response mechanism is arranged to be responsive to the discharge lamp and provides a second electrical response as a function of the electromagnetic energy received from the reference luminescent material. The first response mechanism and the second response mechanism are arranged such that the first electrical response opposes the second electrical response creating a combined output signal. A phase conversion mechanism is coupled to the first and second response mechanisms and convert the amplitude variations of the combined output to phase variations producing a phase output signal. A phase detector is coupled to the phase output signal to detect the phase of the filtered output signal and produce a first response when the filtered output signal is of a first phase and produce a second response when the filtered signal is of a second phase. An indicator is coupled to the phase detector to indicate the condition of the fluorescence of the target luminescent material as a function of at least one of the first response and second response.

The present invention, in an alternative embodiment, provides an apparatus for detecting the fluorescence of a target luminescent material excitable at an excitation wavelength and fluorescing at a fluorescing wavelength. A discharge lamp is adapted to be coupled to an alternating current voltage source and arranged to excite the target luminescent material at approximately the excitation wavelength. A first response mechanism is arranged to be responsive to the target luminescent material at approximately the fluorescing wavelength and provides a first electrical response as a function of the electromagnetic energy received from the target luminescent material at the fluorescing wavelength. A second response mechanism is arranged to be responsive to the discharge lamp and provides a second electrical response as a function of the electromagnetic energy received from the reference luminescent material. The first response mechanism and the second response mechanism are arranged such that the first electrical response opposes the second electrical response creating a combined output signal. An indicator is coupled to the first response mechanism and to second response mechanism and is responsive to the combined output signal to indicate the fluorescence of the target luminescent material based upon the combined output signal.

It is preferred that the phase detector is a rectifier adapted to be coupled to the alternating current voltage source producing a rectified output and a summing mechanism coupled to the band pass filter and to the rectifier for summing the filtered output signal and the rectified output and producing a summed signal wherein a relative high magnitude for the amplitude of the summed signal is indicative of the first response and a relative low magnitude for the amplitude of the summed signal is indicative of the second response.

It is preferred that the apparatus detect the fluorescence of the target luminescent material above a predetermined threshold and which further has an adjustment mechanism coupled to the target luminescent material, to the reference luminescent material, to the first or second photo-diodes or to the discharge lamp for balancing the output of the first and second photo-diodes when the apparatus is measuring a target luminescent material which fluoresces at the predetermined threshold.

It is preferred that the apparatus further has a phase delay coupled between the band pass amplifier and the phase detector to adjust the phase of the filtered output signal to maximize the opposition of the phase of the photo-diode output signal and the rectified signal when the apparatus is measuring a target luminescent material which fluoresces at the predetermined threshold.

BRIEF DESCRIPTION OF THE DRAWINGS

The foregoing advantages, construction and operation of the present invention will become more readily apparent from the following description and accompanying drawings in which.

DETAILED DESCRIPTION OF THE PREFERRED EMBODIMENTS

Figure 1:
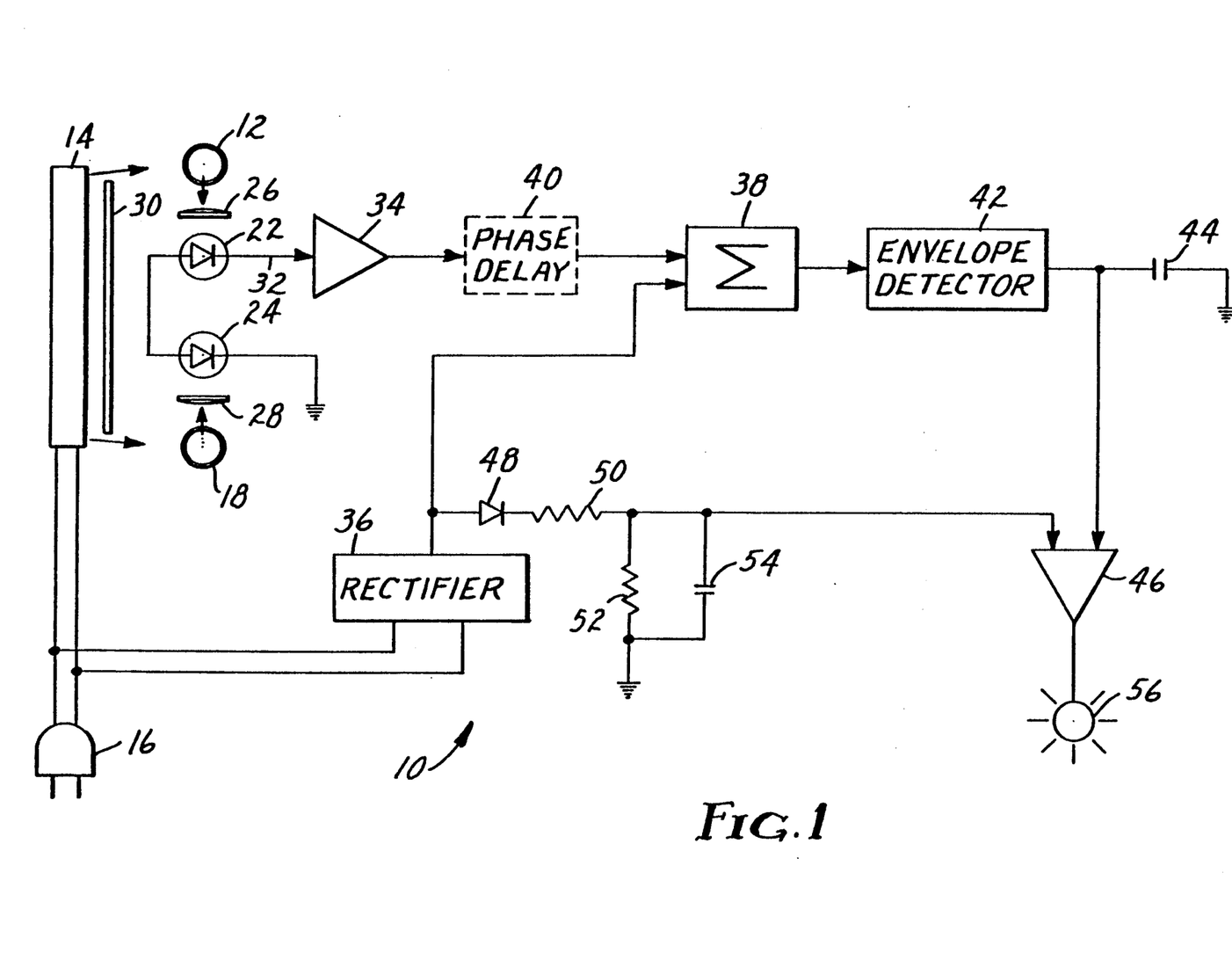
FIG. 1 is a block diagram representation of an embodiment of the apparatus of the present invention.

FIG. 1 illustrates the apparatus 10 of the present invention which is used to detect the fluorescence of a target luminescent material 12. The target luminescent material 12 is tagged to living organisms which are typically contained in a small vial has been inserted into a sterilization unit. The vial has been provided nourishment and an environment for rapid growth after being subjected to the sterilization process. If the sterilization process was complete then the high heat of the sterilization environment will have killed the living organisms which might otherwise contaminate the equipment to be sterilized. If, however, the living organisms have not been killed by the sterilization process then some of the living organisms will remain and the apparatus 10 of the present invention can detect the fluorescence of the remaining target luminescent material 12 tagged to those living organisms. A level of fluorescence above a predetermined amount is indicative of a failed sterilization process.

An example of the type of target luminescent material 12 is material that is capable of undergoing a change to produce fluorescence that is caused by living organisms or enzymes or metabolic by-products utilized in the apparatus 10 is described in U.S. patent application Ser. No. 07/277,305, Mather, Foltz and Woodson, RAPID METHOD FOR DETERMINING EFFICACY OF A STERILIZATION CYCLE AND RAPID READ-OUT BIOLOGICAL INDICATOR, filed Nov. 29, 1988, assigned to the assignee of the present application and which is hereby incorporated by reference. Typically the target luminescent material 12 is excitable at a particular, or several, fluorescing wavelengths.

A discharge lamp 14, typically an ultraviolet lamp, is positioned to, preferably directly, excite the vial containing the target luminescent material 12. The discharge lamp 14 is designed to operate at a fluorescing wavelength in order to excite the target luminescent material 12 so as to produce a wavelength in the visible light region. The discharge lamp 14 is powered from an alternating current voltage source, typically a 60 Hertz power line source as indicated by plug 16. Discharge lamp 4 is arranged to also, preferably directly, excite a reference luminescent material 18. An example of the discharge lamp 14 which could be utilized is the well known series of "BL" fluorescent lamps available from several commercial sources. A preferred discharged lamp 14 is a F4T5BLB lamp available from several manufacturers.

A first photo-diode 22, preferably operating in photo-voltaic mode, is positioned to receive the fluorescence of the target luminescent material 12. A second photo-diode 24, preferably operating in photo-voltaic mode, is positioned to receive the fluorescence of the reference luminescent material 18. Optionally, a first lens 26 may be positioned between the target luminescent material 12 and the first photo-diode 22 in order to improve the collimation of the fluorescing activity. Similarly, an optional second lens 28 may be placed between the reference luminescent material 18 and the second photo-diode 24. Additionally, lens 26 and lens 27 can be chosen as filters to selectively eliminate longer wavelength light such as red and infrared thus rejecting confusing electromagnetic radiation. A shield 30, if required, is provided to prevent the discharge lamp 14 from directly stimulating either the first photo-diode 22 or the second photo-diode 24.

The first photo-diode 22 is designed to be responsive to visible light in the wavelength range of the fluorescence of the target fluorescent material 12. Similarly, the second photo-diode 24 is designed to be responsive to visible light in the wavelength range of the fluorescence of the reference luminescent material. Since, in the preferred mode of operation, the apparatus 10 is designed to detect whether the fluorescence is above a predetermined threshold, it is not required that the electrical characteristics of the first photo-diode 22 be matched to the electrical characteristics of the second photo-diode 24. Although it is preferable if the characteristics are generally similar in order to make the apparatus more linear over a broader range of output, it is enough, especially in a threshold device, that the characteristics can be adjusted for the range of the expected threshold value. Thus, first and second photo-diodes (22 and 24) need not be matched at all. In the preferred embodiment, an actual photo-diode is utilized for the first photo-diode 22 while a photo-transistor operating as a photo-diode is utilized for second photo-diode 24. A photo-transistor is used because it is inherently less expensive and since the measurement from the luminescent reference is subject to adjustment in order to closely match the characteristics at the threshold value. The preferred first photo-diode 22 is a SD—041—1—2—12—211 available from the United Detector Technology and the preferred second photo-diode (actually a photo-transistor operating as a photo-diode) 24 is a L14N2 available from General Electric. It is not particularly important that these elements be photo-diodes, photo-transistors or something else, as long as they respond to visible light in the frequency range of the fluorescence of the luminescent materials and produce an electrical output in response thereto. Preferably the electrical response evoked is a voltage across the element or the output of the element.

While the target luminescent material 12 is contained in the vial possibly containing the living organisms, such an elaborate material is not required for the reference luminescent material 18. In the preferred embodiment, the reference luminescent material 18 is simply a piece of material, e.g., cardboard, which is covered with a paint in order to produce a visible response to the ultraviolet light of the discharge lamp 14 similar to the fluorescent spectrum of the target luminescent material 12.

While the electrical characteristics of the first photo-diode 22 and the second photo-diode 24 are not particularly critical, in one aspect of the invention the electrical connection of these elements is critical. First photo-diode 22 and second photo-diode 24 are electrically connected "back-to-back", i.e., electrically connected in series with ground but oppositely oriented, so that the voltage produced by one of the photo-diodes (22 or 24) will be directly offset by the other of the photo-diodes (24 or 22, respectively). Since the voltages produced offset each other the voltage appearing across both photo-diodes (22 and 24) will be the resultant voltage of any difference of voltages between photo-diodes 22 and 24. In fact, it is preferred that the apparatus 10 be adjusted so that the net voltage output of the photo-diodes is approximately zero at the threshold condition.

Figure 2:
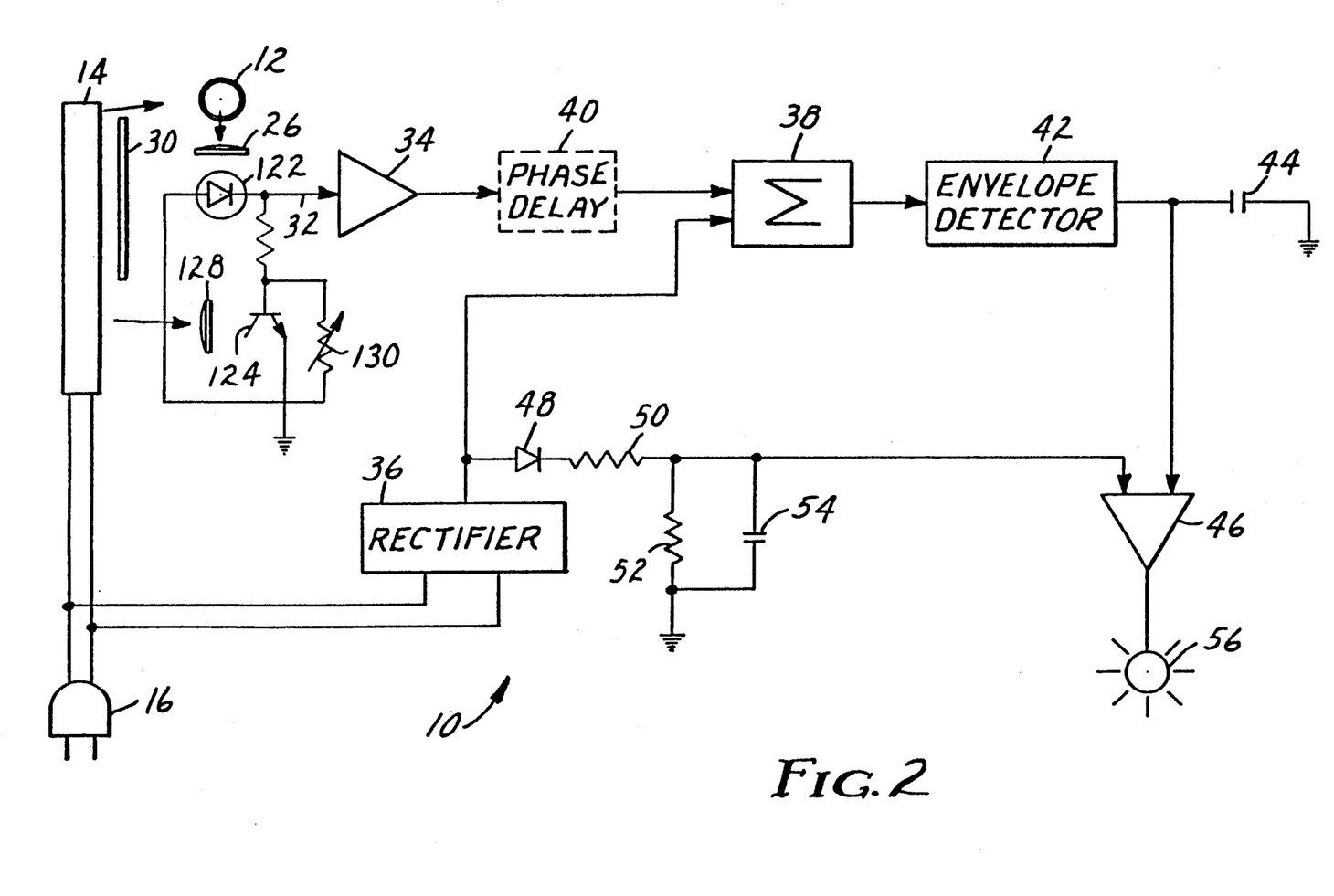
FIG. 2 is a block diagram representation of the preferred embodiment of the apparatus of the present invention.

Alternatively, first and second photo-diodes (122 and 124) can be connected in parallel with each but with opposite orientations with respect to ground, as illustrated in FIG. 2, to gain greater sensitivity for the apparatus 10.

The apparatus 10 is adjusted as discussed above by varying the output of photo-diode 24 (which measures the reference luminescent material 18). The electrical output of photo-diode 24 can be adjusted by varying its physical distance from reference luminescent material 18 or by partial masking of the light impinging on the diode or by addition of a shunting resistor. This can be accomplished, e.g., by an adjustment screw, or slug, which moves the mount of reference luminescent material 18 in relation to photo-diode 24. However positioned, or adjusted, reference luminescent material 18 provides a stable reference luminescent value against which the threshold determination of the apparatus 10 of the present invention can be made.

While the electrical characteristics of the first photo-diode 22 and the second photo-diode 24 are not matched, it is expected that satisfactory performance of the apparatus 10 could be obtained over a limited range of fluorescence if an actual measurement of fluorescence were desired rather than a threshold indication.

With photo-diodes 22 and 24 (or 122 and 124) connected "back-to-back" as shown in FIG. 1 (or, alternatively, in "parallel oppositely oriented" arrangement as shown in FIG. 2), the photo-diodes 22 and 24 (or 122 and 124) produce canceling currents (or voltages) and a net zero voltage output on line 32 (with respect to ground) at threshold condition regardless of the amplitude of the ultraviolet light produced by the discharge lamp 14.

While in the preferred embodiment of the invention, a single discharge lamp 14 is utilized which excites both the target luminescent material 12 and the reference luminescent material 18, it is not necessary that a single discharge lamp be used in order to obtain all of the advantages of the present invention. Separate discharge lamps (analogous to discharge lamp 14) could be used to stimulate the luminescent materials (12 and 18). Although each discharge lamp might vary in the level of radiation produced, this variation could be compensated for in the adjustment procedures discussed above. Each discharge lamp, preferably, would be connected to the same power source. Thus, variations of the level of power provided to the discharge lamps would be the same and similar changes in the level of radiation output of the discharge would occur.

Photo-diodes 22 and 24 have been described as being connected "back-to-back". Other connection arrangements are also contemplated. In one embodiment of the invention, these other connection arrangements must result in the opposition of the electrical response of photo-diode 22 by the electrical response of photo-diode 24, or, in other words, the electrical response evoked by the target luminescent material 12 must oppose the electrical response evoked by the reference luminescent material 18. At threshold condition this would result in the cancellation of the electrical responses and a net zero combined output signal 32. The "back-to-back" connection of the photo-diodes 22 and 24 allows a single amplification channel can be used for the combined output signal 32. Since only a single amplification channel is required, dual amplification channels involving the either the possibility of mismatched components and resulting inaccurate measurements or very costly matching of components between the dual channels.

At the threshold condition of the apparatus 10, the combined output signal 32 from the photo-diodes will be extremely small due to the opposition of the electrical responses. If the evoked electrical response from target luminescent material 12 is slightly greater than the evoked electrical response from the reference luminescent material 18, indicating the presence of fluorescence in the target vial having greater than allowed living organisms due to an insufficient sterilization process, then the combined output signal 32 will be slightly positive (or negative depending upon the connection). Conversely, if the evoked electrical response from target luminescent material 12 is slightly smaller than the evoked electrical response from the reference luminescent material 18, indicating the presence of fluorescence in the target vial having less than the allowed living organisms due to a proper sterilization process, then the combined output signal 32 will be slightly negative (or positive depending upon the connection).

Since the combined output signal 32 in the near threshold condition is very small in amplitude, it must be greatly amplified. Because of the very low amplitude levels involved, DC drift generally can cause the signal to be swamped with the result that the threshold would move randomly. This would cause uncertain detection and result in inaccurate results. AC coupling, instead of the more normal DC coupling, would solve the DC drift problem but, alas, would also swamp the low level DC signal being detected.

In one aspect of the invention, this problem is solved by utilizing a detection of the phase of the combined output signal 32. Since the photo-diodes 22 and 24 are connected oppositely, if the electrical output from one photo-diode predominates the combined output signal 32 will be of one phase and, conversely, if the electrical output of the other photo-diode predominates then the combined output signal 32 will be of the opposite phase. Thus, a detector which examines the phase of the combined output signal 32 can determine which luminescent material (12 or 18) fluoresces more, thus determining whether the target luminescent material fluoresces above or below the threshold amount. In fact, it is not necessary to know what the phase of the combined output signal 32 is, but merely to know whether the phase of the combined output signal 32 changes from when the target luminescent material 12 is removed from the apparatus 10 as compared to when the target luminescent material 12 is inserted into the apparatus 10. If the phase of the combined output signal 32 does not change upon insertion, then the electrical output signal from the reference luminescent material 18 still prevails, then the fluorescence from the reference luminescent material 18 exceeds the fluorescence from the target luminescent material 12 and the sterilization process passes. However, if the phase of the combined output signal 32 changes upon insertion, then the electrical output signal from the target luminescent material 12 prevails, the fluorescence from the target luminescent material 12 exceeds the fluorescence from the reference luminescent material 18 and the sterilization process fails.

In a preferred embodiment of the invention, the phase of the combined output signal 32 is compared to a signal of known phase, namely the phase of the line voltage signal. Thus, it is not necessary to watch for a phase change when the target luminescent material 12 is inserted into or removed from the apparatus 10. The apparatus can determine whether the phase of the combined output signal 32 matches the condition of greater fluorescence of the target luminescent material 12 or the condition of greater fluorescence of the reference luminescent material 18.

The combined output signal 32 is amplified in operational amplifier 34. While, in general, any amplification circuit can be utilized, in one aspect of the present invention, operational amplifier 34 is a 120 Hertz bandpass amplifier, e.g., one portion of a 34002 by Motorola.

Optionally, a 500 megohm feedback resistor (not shown) can be connected between input and output of operational amplifier 34. Fluorescent lamps, the type of lamp usually utilized for discharge lamp 14, being connected to an alternating current type line voltage source, will oscillate at line frequency, typically 60 Hertz. Experience has shown that fluorescent lamps produce a very large modulation component at twice the line frequency (the second harmonic), namely 120 Hertz in this instance. Experience has also shown that the second harmonic is also fairly stable. In fact, the second harmonic is the most stable component of the various harmonics of the line frequency. The fundamental component, the 60 Hertz component, is essentially unusable because there is little control over how much fundamental is present. Due to variations in the filaments of the fluorescent lamp, the fluorescent lamp may ionize at one end more than at the other which causes great fluctuations in the amount of fundamental component available. In fact, if the filaments of the fluorescent lamp were to match exactly, they would cancel and there would no fundamental (60 Hertz) component at all. The second harmonic, however, is fundamentally stable since each end of the filaments of the fluorescent lamp will produce a second harmonic which will not cancel the second produce from the opposite end of the fluorescent lamp. Higher harmonics, however, are intrinsically unstable in phase and amplitude because they are strongly dependent upon plasma events in the fluorescent lamp.

By using operational amplifier 34, the apparatus 10 stages can be AC decoupled eliminating any DC drift problem.

The phase of the output from operational amplifier 34 is then compared to the phase of the line voltage source coming from plug 16. A 120 Hertz (actually twice the line frequency) line generator 36 is coupled directly to the line voltage source (from plug 16). A simple preferred example of the 120 Hertz line generator 36 is a commonly available full-wave rectifier. Optionally, a phase locked loop may be utilized. Thus, the output of the 120 Hertz line generator 36 provides a ready reference, a phase locked electrical reference, against which the output from operational amplifier 34 can be compared. Both signals are supplied to summer 38 which adds the output from operational amplifier 34 t the output from the 120 Hertz line generator. Since in one phase condition the signals will reinforce each other when added, and in the opposite phase condition the signals will oppose each other, the output of summer 38 represents an amplitude response to the phase comparison. Summer 38, in conjunction with 120 Hertz line generator, operates to convert the phase information contained in the output of operational amplifier 34 to amplitude information. In a preferred embodiment, summer 38 may be one portion of a 34002 by Motorola Optionally, a phase delay 40 may be inserted between the output of operational amplifier 34 and the input of summer 38. Phase delay 40 may be used to bring one the phases of the output signal from the operational amplifier 34 into coincidence with the electrical reference signal from the 120 Hertz line generator 36. There is inherently some phase delay in operational amplifier 34 (since it includes a 120 Hertz bandpass filter) and there is some phase delay in the 120 Hertz line generator 36. In order to ensure that the signals appearing at summer 38 actually oppose or reinforce each other, the signals are looked at intrinsically on an oscilloscope and phase delay 40 adjusted to achieve opposition and reinforcement. Typically, phase delay 40 may be constructed as a resistive-capacitive network. In a preferred embodiment, phase delay 40 is constructed from a 10 kilohm series resister and a 47 microfarad shunt capacitor.

The output from summer 38, having amplitude information, is fed directly to envelope detector 42. Envelope detector 42 detects the envelope of the signal, i.e., the peaks of the signal, and provides an output when the signals reaches the threshold value (determined intrinsically). Envelope detector 42 may be any of many well known envelope detectors commonly available and, in one embodiment, may be a diode peak detector and a low pass filter. In a preferred embodiment, envelope detector 42 is formed with a pair of 1N414B- diodes and a low pass filter constructed from a 10 kilohm-resistor and a 2.2 microfarad capacitor. Capacitor 44, preferably 2.2 microfarads, eliminates any AC variations still present at the output of envelope detector 42. Capacitor 44 also forms part of the low pass filter portion of envelope detector 42.

The output from envelope detector 42 is fed to a comparator 46 which compares the amplitude of the signal with a signal having a level based upon the amplitude of the line voltage. Diode 48, connected to the output of 120 Hertz line generator 36, provides a half-wave rectified signal from the line voltage source. This half-wave rectified signal, of course, has a DC component directly related to the amplitude of the AC line voltage source. Resistors 50 and 52 provide a voltage division to provide a proper level of signal for comparison at comparator 46. In a preferred embodiment comparator 46 is one portion of a 34002 by Motorola. Capacitor 54 eliminates any AC component remaining. Through proper selection, intrinsically, of resistors 50 and 52, comparator 46 provides a comparison of the signal from the envelope detector 42 with the amplitude of the line voltage source. Since the output of the envelope detector can vary substantially due to line voltage variations, comparator 46 can eliminate these variations. Comparator 46 may be any of many well known comparators and, in a preferred embodiment, may be a FET (field effect transistor) input operational amplifier operated with hystersis. Resistors 50 and 52, preferably, are chosen to create a comparative balance at the desired measurement threshold and valued at 1 megohm and 200 kilohms, respectively.

In a preferred embodiment, a single Motorola 34002 circuit provides operational amplifier 34, summer 38 and comparator 46.

The output from comparator 46 is dependent on the amount of fluorescence detected from the target luminescent material 12 and is used to drive an indicator. In a preferred embodiment, the indicator 56 is simply a light which indicates a fluorescence of the target luminescent material 12 above, or below, threshold indicating a sterilization process which has failed, or which passes, respectively. Other indicators such as a meter, digital read-out or audible alarm could also be used.

FIG. 2 illustrates the preferred embodiment of the apparatus 10A of the present invention which is used to detect the fluorescence of a target luminescent material 12. As in FIG. 1, a discharge lamp 14, typically an ultraviolet lamp, is positioned to, preferably directly, excite the vial containing the target luminescent material 12. The discharge lamp 14 is designed to operate at a fluorescing wavelength in order to excite the target luminescent material 12 so as to produce a wavelength in the visible light region. The discharge lamp 14 is powered from an alternating current voltage source, typically a 60 Hertz power line source as indicated by plug 16. An example of the discharge lamp 14 which could be utilized is the well known series of "BL" fluorescent lamps available from several commercial sources. A preferred discharged lamp 14 is a F4-T-5BLB lamp available from several manufacturers. A first photo-semiconductor 122, preferably a photodiode operating in photo-voltaic mode, is positioned to receive the fluorescence of the target luminescent material 12. A shield 30 is provided to prevent discharge lamp 14 from directly stimulating the first photo-semiconductor 122. Optionally, a first lens 26 may be positioned between the target luminescent material 2 and the first photo-semiconductor 122 in order to improve the collimation of the fluorescing activity.

However, in the preferred embodiment of the apparatus of the present illustrated in FIG. 2, discharge lamp 14 is arranged to directly excite photo-semiconductor 102. The second photo-semiconductor 24 is preferably a photo-transistor since the input stimulation level of the photo-semiconductor is relatively greater due to the direct stimulation from the discharge lamp 14. Preferably the second photo-semiconductor operates in photo-voltaic mode. An optional second lens 128, preferably a KG5 infrared filter from Schott Glass Works, Rochester, New York, may be placed between the discharge lamp 14 and the second photo-semiconductor 124 to improve the collimation of the signal from the discharge lamp 14.

As in FIG. 1, lens 26 and lens 128 can be chosen as filters to selectively eliminate longer wavelength light such as red and infrared thus rejecting confusing electromagnetic radiation.

The first photo-semiconductor 122 is designed to be responsive to visible light in the wavelength range of the fluorescence of the target fluorescent material 12. The second photo-semiconductor 124 is designed to be responsive to light in the wavelength range of the discharge lamp 14. It is not required that the electrical characteristics of the first photo-semiconductor 122 be matched to the electrical characteristics of the second photo-semiconductor 124. Although it is preferable if the characteristics are generally similar in order to make the apparatus more linear over a broader range of output, it is enough, especially in a threshold device, that the characteristics can be adjusted for the range of the expected threshold value. Thus, first and second photo-semiconductors (22 and 124) need not be matched at all. In the preferred embodiment, a photo-diode is utilized for the first photo-semiconductor 122 while a photo-transistor operating as a photo-semiconductor is utilized for second photo-semiconductor 124. The preferred first photo-semiconductor 122 is a SD-041-12-12-211 available from the United Detector Technology. The preferred second photo-semiconductor (actually a photo-transistor operating as a photo-semiconductor) 124 is a L14N2 available from General Electric. It is not particularly important that these elements be photo-semiconductors, photo-transistors or something else, as long as they respond to light in the frequency range of to be detected and produce an electrical output in response thereto. Preferably, the electrical response evoked is a voltage across the element or the output of the element.

First photo-semiconductor 122 and second photo-semiconductor 124 are connected so that the output voltage which each produces will oppose the other. The first and second photo-semiconductors (122 and 124) are electrically connected in parallel with each other but oppositely oriented, so that the voltage produced by one to the photo-semiconductors (122 or 124) will be directly offset by the other of the photo-semiconductors (124 or 122, respectively). Resistor 132 (22 megohms) is coupled in series with photo-semiconductor 124. Since the voltages produced offset each other, the voltage appearing across both photo-semiconductors (122 and 124) will be the resultant voltage of any difference of voltages between photo-semiconductors 122 and 124. In fact, it is preferred that the apparatus 10A be adjusted so that the net voltage output of the photo-semiconductors is approximately zero at the threshold condition.

With photo-semiconductors 122 and 124 connected with opposing electrical characteristics as shown in FIG. 2, the photo-semiconductors 122 and 124 produce canceling voltages and a net zero voltage output on line 32 (with respect to ground) at threshold condition regardless of the amplitude of the ultraviolet light produced by the discharge lamp 14.

This arrangement of the first photo-semiconductor 122 and second photo-semiconductor 124 helps eliminate problems of component mismatch, uneven aging and temperature related changes of the components. The current produced by the first photo-semiconductor 122 is not required to flow through the high impedance of the second photo-semiconductor thus improving the sensitivity of the detecting circuitry while maintaining compensation for ambient temperature and compensation for variations in the output of the discharge lamp 14.

The apparatus 10A can be adjusted by varying the resistance of variable resistor 130 (2 kilohm potentiometer) coupled between the base and emitter of photo-semiconductor 124. Typically, resistor 130 is adjusted at and preset at the factory. In addition, the electrical output of photo-semiconductor 124 can be adjusted by varying its physical relationship with respect to discharge lamp 14 or by partial masking of the light impinging on the diode. However positioned, or adjusted, second photo-semiconductor 124 provides a stable reference value against which the threshold determination of the apparatus 10A can be made.

If the apparatus 10A were constructed to obtain an actual measurement of fluorescence, rather than a threshold indication, it is expected that satisfactory performance could be obtained over a limited range of fluorescence even though the electrical characteristics of the first photo-semiconductor 122 and the second photo-semiconductor 124 were not matched.

While in the preferred embodiment of the invention, a single discharge lamp 14 is utilized which excites both the target luminescent material 12 and second photo-semiconductor 124, it is not necessary that a single discharge lamp be used in order to obtain all of the advantages of the present invention. Separate discharge lamps (analogous to discharge lamp 14) could be used to stimulate the target luminescent material 12 and the second photo-semiconductor 124, respectively. Although each discharge lamp might vary in the level of radiation produced, this variation could be compensated for in the adjustment procedures discussed above. Each discharge lamp, preferably, would be connected to the same power source. Thus, variations of the level of power provided to the discharge lamps would be the same and similar changes in the level of radiation output of the discharge lamps would occur.

Photo-semiconductors 122 and 124 have been described as being connected in parallel with each but oppositely oriented. Other connection arrangements are also contemplated, such as the "back-to-back" arrangement discussed with respect to the apparatus 10 described in FIG. 1. These other connection arrangements result in the opposition of the electrical response of photo-semiconductor 122 by the electrical response of photo-semiconductor 128, or, in other words, the electrical response evoked by the target luminescent material 12 must oppose the electrical response evoked by the discharge lamp itself. At threshold condition this would result in the cancellation of the electrical responses and a net zero combined output signal 32. The "parallel-oppositely oriented" connection of the photo-semiconductors 122 and 128 allows a single amplification channel to be used for the combined output signal 32. Since only a single amplification channel is required, dual amplification channels involving the either the possibility of mismatched components and resulting inaccurate measurements or very costly matching of component between the dual channels is avoided.

At the threshold condition of the apparatus 10A, the combined output signal 32 from the photo-semiconductors (122 and 124) will be extremely small due to the opposition of the electrical responses. If the evoked electrical response from target luminescent material 12, and, hence, first photo-semiconductor 122, is slightly greater than the evoked electrical response from the second photo-semiconductor 128, indicating the presence of fluorescence in the target vial having greater than allowed living organisms due to an insufficient sterilization process, then the combined output signal 32 will be slightly positive (or negative depending upon the connection). Conversely, if the evoked electrical response from target luminescent material 12, and, hence, first photo-semiconductor 122, is slightly smaller than the evoked electrical response from the second photo-semiconductor 124, indicating the presence of fluorescence in the target vial having less than the allowed living organisms due to a proper sterilization process, then the combined output signal 32 will be slightly negative (or positive depending upon the connection).

The remainder of the circuitry illustrated in FIG. 2, namely operational amplifier 34, 120 Hertz line generator 36, summer 38, phase delay 40, envelope detector 42, capacitor 44, comparator 46, diode 48, resistor 50, resistor 52, capacitor 54 and indicator 56, are the equivalent of the corresponding components in described with respect to FIG. 1.

Thus, it can be seen that there has been shown and described a novel apparatus for detecting the fluorescence of a luminescent material. It is to be recognized and understood, however, that various changes, modifications and substitutions in the form and the details of the present invention may be made by those skilled in the art without departing from the scope of the invention as defined by the following claims.

What is claimed is:

1. An apparatus for detecting the fluorescence of a target luminescent material being excitable at an excitation wavelength and fluorescing at a fluorescing wavelength, comprising:

a discharge lamp adapted to be coupled to an alternating current voltage source operating at a source frequency and arranged to excite said target luminescent material at approximately said excitation wavelength;

first response means arranged to be responsive to said target luminescent material at approximately said fluorescing wavelength for providing a first electrical response as a function of the electromagnetic energy received from said target luminescent material at said fluorescing wavelength;

second response means arranged to be responsive to said discharge lamp for providing a second electrical response as a function of the electromagnetic energy received from said discharge lamp;

said first response means and said second response means being arranged such that said first electrical response opposes said second electrical response creating a combined output signal;

a band pass filter coupled to said combined output signal selected to pass predominantly signals of a frequency of approximately twice said source frequency to produce a filtered output signal;

a phase detector coupled to said band pass filter to detect the phase of said filtered output signal and producing a first response when said filtered output signal is of a first phase and producing a second response when said filtered signal is of a second phase; and an indicator coupled to said phase detector to indicate the condition of said fluorescence of said target luminescent material as a function of at least one of said first response and second response.

2. An apparatus for detecting fluorescence as in claim 1 wherein said first response means and said second response means comprise first and second photo-semiconductors operating in photo voltaic mode, said first and second photo-semiconductors being oppositely coupled in parallel.

3. An apparatus for detecting fluorescence as in claim 1 wherein said phase detector comprises:
a rectifier adapted to be coupled to said alternating current voltage source producing a rectified output;
summing means coupled to said band pass filter and to said rectifier for summing said filtered output signal and said rectified output and producing a summed signal wherein a relative high magnitude for the amplitude of said summed signal is indicative of said first response and a relative low magnitude for the amplitude of said summed signal is indicative of said second response.

4. An apparatus for detecting fluorescence as in claim 3 wherein said phase detector further comprises an alternating current voltage source comparator coupled between said summing mean and said indicator which compares the magnitude of the amplitude of said summed signal to the magnitude of the voltage amplitude of said alternating current voltage source and produces said first response as a function of the magnitude of amplitude of said line voltage.

5. An apparatus for detecting fluorescence as in claim 3 wherein said apparatus detects said fluorescence of said target luminescent material above a predetermined threshold and which further comprises an adjustment means coupled to said target luminescent material, to said first or second photo-semiconductors or to said discharge lamp for balancing the output of said first and second photo-semiconductors when said apparatus is measuring a target luminescent material which fluoresces at said predetermined threshold.

6. An apparatus for detecting fluorescence as in claim 5 which further comprises a phase delay coupled between said band pass amplifier and said phase detector to adjust the phase of said filtered output signal to maximize the opposition of the phase of said photo-semiconductor output signal and said rectified signal when said apparatus is measuring a target luminescent material which fluoresces at said predetermined threshold.

7. An apparatus for detecting the fluorescence of a target luminescent material being excitable at an excitation wavelength and fluorescing at a fluorescing wavelength comprising:
a discharge lamp adapted to be coupled to an alternating current voltage source operating at a source frequency and arranged to excite said target luminescent material at approximately said excitation wavelength;
first response means arranged to be responsive to said target luminescent material at approximately said fluorescing wavelength for providing a first electrical response as a function of the electromagnetic energy received from said target luminescent material at said fluorescing wavelength;
second response means arranged to be responsive to said discharge lamp for providing a second electrical response as a function of the electromagnetic energy received from said discharge lamp;
said first response means and said second response means being arranged such that said first electrical response opposes said second electrical response creating a combined output signal;
phase conversion means coupled to said first and second response means for converting amplitude variations of said combined output signal to phase variations producing a phase output signal;
a phase detector coupled to said phase output signal to detect the phase of said filtered output signal and producing a first response when said filtered output signal is of a first phase and producing a second response when said filtered signal is of a second phase; and
an indicator coupled to said phase detector to indicate the condition of said fluorescence of said target luminescent material as a function of at least one of said first response and second response.

8. An apparatus for detecting fluorescence as in claim 7 wherein said first response means and said second response means comprise first and second photo-semiconductors operating in photo voltaic mode, said first and second photo-semiconductors being oppositely coupled in parallel.

9. An apparatus for detecting fluorescence as in claim 7 wherein said phase detector comprises:
a rectifier adapted to be coupled to said alternating current voltage source producing a rectified output;
summing means coupled to said phase converter and to said rectifier for summing said filtered output signal and said rectified output and producing a summed signal wherein a relative high magnitude for the amplitude of said summed signal is indicative of said first response and a relative low magnitude for the amplitude of said summed signal is indicative of said second response.

10. An apparatus for detecting fluorescence as in claim 9 wherein said phase detector further comprises an alternating current voltage source comparator coupled between said summing means and said indicator which compares the magnitude of the amplitude of said summed signal to the magnitude of the voltage amplitude of said alternating current voltage source and produces said first response as a function of the magnitude of amplitude of said line voltage.

11. An apparatus for detecting fluorescence as in claim 7 wherein said apparatus detects said fluorescence of said target luminescent material above a predetermined threshold and which further comprises an adjustment means coupled to said first or second photo-semiconductor or to said discharge lamp for balancing the output of said first and second photo-semiconductors when said apparatus is measuring a target luminescent material which fluoresces at said predetermined threshold.

12. An apparatus for detecting the fluorescence of a target luminescent material being excitable at an excitation wavelength and fluorescing at a fluorescing wavelength comprising:
a discharge lamp adapted to be coupled to an alternating current voltage source arranged to excite said target luminescent material at approximately said excitation wavelength;
first response means arranged to be responsive to said target luminescent material at approximately said fluorescing wavelength for providing a first electrical response as a function of the electromagnetic energy received from said target luminescent material at said fluorescing wavelength;
second response means arranged to be responsive to said discharge lamp for providing a second electrical response as a function of the electromagnetic energy received from said discharge lamp;
said first response means and said second response means being arranged such that said first electrical response directly offsets said second electrical response creating a combined output signal;
an indicator coupled to said first response means and to second response means and responsive to said combined output signal to indicate the fluorescence of said target luminescent material based upon said combined output signal.

13. An apparatus for detecting fluorescence as in claim 12 wherein said first response means and said second response means comprise first and second photo-semiconductors operating in photo voltaic mode, said first and second photo-semiconductors being oppositely coupled in parallel.

14. An apparatus for detecting fluorescence as in claim 12 wherein said apparatus detects said fluorescence of said target luminescent material above a predetermined threshold and which further comprises an adjustment means coupled to said first or second photo-semiconductors or to said discharge lamp for balancing the output of said first and second response means when said apparatus is measuring a target luminescent material which fluoresces at said predetermined threshold.

* * * * *

UNITED STATES PATENT AND TRADEMARK OFFICE
CERTIFICATE OF CORRECTION

PATENT NO. : 5,063,297

DATED : November 5, 1991

INVENTOR(S) : James M. Hardenbrook, Richard E. Williams, and Mark L. Daniel

It is certified that error appears in the above-identified patent and that said Letters Patent is hereby corrected as shown below:

```
Col. 1, line 48, "!hen" should read --then--.
Col. 2, line 67, "canceled" should be followed by a comma.
Col. 10, line 46, "t" should read --to--.

Col. 11, line 15, "1N414B-" should read --1N414B--.

Col. 12, line 7-8, "F4-T5BLB" should read --F4T5BLB--.

Col. 12, line 15, "2" should read --12--.

Col 12, line 21, "24" should read --124--.

Col. 15, line 55, "mean" should read --means--.
```

Signed and Sealed this

Twenty-eighth Day of September, 1993

Attest:

BRUCE LEHMAN

*Attesting Officer*   *Commissioner of Patents and Trademarks*